United States Patent [19]

Matsumura et al.

[11] 4,336,374

[45] Jun. 22, 1982

[54] QUATERNARY AMMONIUM SUBSTITUTED N-CINNAMYLPIPERIDINES

[75] Inventors: Shingo Matsumura, Kyoto; Hiroshi Enomoto, Nagaokakyo; Yoshiaki Aoyagi, Otsu; Yoshiaki Yoshikuni, Uji; Masahiro Yagi, Kusatsu; Kohei Kura, Omi-Yahata; Ichiro Shirahase, Kyoto, all of Japan

[73] Assignee: Nippon Shinyaku Co., Ltd., Japan

[21] Appl. No.: 247,884

[22] Filed: Mar. 26, 1981

Related U.S. Application Data

[63] Continuation-in-part of Ser. No. 229,277, Jan. 28, 1981, abandoned.

[30] Foreign Application Priority Data

Jan. 28, 1980 [JP] Japan ................................. 55-9174

[51] Int. Cl.$^3$ .......................................... C07D 211/46
[52] U.S. Cl. ................................... 542/469; 424/267; 542/447; 546/243

[58] Field of Search ................. 542/469, 447; 546/243

[56] References Cited

U.S. PATENT DOCUMENTS 4,182,767 1/1980 Murai et al. ......................... 546/242
4,220,782 9/1980 Stoltefuss et al. ................... 546/242

OTHER PUBLICATIONS

Matsumura et al., Chem. Abst. 92 (1980) #147138 and 110857.

Primary Examiner—Arthur P. Demers
Attorney, Agent, or Firm—Jacobs & Jacobs

[57] ABSTRACT

2-Hydroxymethyl-3,4,5-trihydroxypiperidines bearing a quaternary ammonium-substituted cinnamyl group on the piperidine nitrogen atom and their acid addition salts are antihyperglycemic agents. A typical example is 1-(4-trimethylammoniumcinnamyl)-2-hydroxymethyl-3,4,5-trihydroxypiperidine chloride.

12 Claims, No Drawings

QUATERNARY AMMONIUM SUBSTITUTED N-CINNAMYLPIPERIDINES

CROSS-REFERENCE

This is a continuation-in-part of Ser. No. 229,277 filed Jan. 28, 1981, now abandoned.

DETAILED DESCRIPTION

This invention relates to the compounds of the formula:

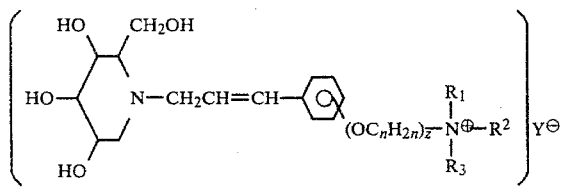

wherein
n has a value of 2 or 3,
z has a value of 0 or 1,
$R^1$ is alkyl of 1 to 6 carbon atoms, each of $R^2$ and $R^3$ is alkyl of 1 to 6 carbon atoms or
$R^2$ and $R^3$ when taken together, together with the nitrogen atom to which they are bound, are 1-morpholinylidene, 1-pyrrolidinylidene or 1-piperidinylidene, i.e., the 1,1-divalent residue of morpholine, pyrrolidine or piperidine; and
$Y^\ominus$ is a pharmaceutically acceptable cation.

The group Y can be substantially any physiologically acceptable anion derived from acids commonly utilized to form quaternary salts as for example sulfate bromide, iodide, chloride and the like.

The compounds can also form acid addition salts by reason of the basic piperidine nitrogen atom. Physiologically acceptable nontoxic acid addition salts of this type include those derived from organic and inorganic acids such as hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The groups $R^1$, $R_2$ and $R^3$ can be the same or different alkyl group such as methyl, ethyl, propyl, isopropyl, butyl and the like. Alternatively, $R^2$ and $R^3$ can form, together with the nitrogen atom to which they are attached, a heterocyclic ring such as pyrrolidine, piperidine or morpholine, in which case $R^1$ is alkyl.

The quaternary group can be directly bound to the phenyl group (z=0) or through an alkyleneoxy bridge (z=1) which may be ethyleneoxy (n=2) or trimethyleneoxy (n=3). In all of these situations, the position of substitution on the phenyl ring may be ortho, meta, or para.

The compounds of this invention and their salts are antihyperglycemic agents and medicinally useful. The property manifests itself through inhibition of an increase of blood sugar in humans and other animals following administration of carbohydrates. Because of other strong inhibition on blood sugar level increase, the compounds are very useful as prophylactic and therapeutic agents for hyperglycemic conditions encountered in, for example, diabetes, arteriosclerosis, obesity, gastritis, peptic ulcer, duodenum ulcer, and the like. The toxicity of the compounds is extremely favorable. At a dose of 5000 mg/kg p.o. in the mouse none of these compounds produced any mortality.

The compounds of the present invention are generally administered orally in any of the usual pharmaceutical forms. These include solid and liquid oral unit dosage forms such as tablets, capsules, powders, suspensions, solutions, syrups and the like, including sustained release preparations. The term unit dosage form as used in this specification and the claims refer to physically discrete units to be administered in single or multiple dosage to animals, each unit containing a predetermined quantity of the piperidine derivative in association with the required diluent, carrier or vehicle. The quantity of the piperidine derivative is that calculated to produce the desired antihyperglycemic effect upon administration of one or more of such units.

Powders are prepared by comminuting the compound to a suitable fine size and mixing with a similarly comminuted diluent pharmaceutical carrier. Although this can be an edible carbohydrate material, as for example starch, generally such are avoided in view of the pharmaceutical use. Flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the piperidine compound, suitably comminuted, with a diluent or base such as kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, polymeric material and a polish coating of wax can be provided. Dyestuffs can be added to these coatings to distinguish different unit dosages.

Oral fluids such as elixirs can be prepared in unit dosage form so that a given quantity, e.g., a teaspoonful, contains a predetermined amount of the compound. Suspensions can be formulated by dispersing the compound in a nontoxic vehicle in which it is insoluble.

The compounds can also be administered in foodstuffs to minimize increases in blood sugar.

The compounds can also be given to livestock, by admixture with their feed, in their drinking water or by conventional veterinary formulations.

The compounds are administered in the conventional manner to humans and other animals, in each case carefully titrating the dose to the age, condition and response of the recipient.

The antihyperglycemic activity can be conveniently observed in well-known and widely employed laboratory models, as for example the depression of blood sugar levels in glucose loaded rats. The compounds all show a percent inhibition of more than 80% when they are orally administered to rats in a dose of 1 mg/kg together with 2 g/kg of sucrose and the percent inhibition of blood sugar level increase is measured 30 minutes later. The following data are representative:

| Compound ($Y^\ominus=Cl^\ominus$, HCl salt) | | | | | | | % |
|---|---|---|---|---|---|---|---|
| No. | o, m, or p | z | n | $R^1$ | $R^2$ | $R^3$ | Inhibition |
| 1 | m | 0 | — | Me | Me | Me | 90 |
| 2 | p | 0 | — | Me | Me | Me | 102 |
| 3 | p | 0 | — | Et | Me | Et | 88 |
| 4 | m | 1 | 2 | Et | Et | Et | 83 |
| 5 | m | 1 | 2 | Me | Me | Me | 87 |
| 6 | m | 1 | 3 | Me | Me | Me | 91 |
| 7 | m | 1 | 2 | Me | —(CH$_2$)$_2$O(CH$_2$)$_2$— | | 93 |
| 8 | m | 1 | 2 | Me | —(CH$_2$)$_5$— | | 83 |
| 9 | p | 1 | 2 | Me | —(CH$_2$)$_4$— | | 87 |

In synthesizing these compounds, 2-hydroxymethyl-3,4,5-trihydroxypiperidine, which is known as moranoline, with or without protection of the hydroxy groups by a suitable group such as an acetyl, benzoyl, benzyl, tetrahydropyranyl, methoxymethyl or methoxyethoxymethyl group, is allowed to react with an activated derivative of cinnamyl alcohol already carrying a quaternary ammonium group. Such activated derivatives include a cinnamyl halide and a cinnamyl sulfuric acid, phosphoric acid or sulfonic acid ester. This N-substitution reaction is carried out in a polar aprotic solvent such as DMF or DMSO or in a lower alkanol in the presence of a suitable acid acceptor such as potassium carbonate or sodium hydrogen carbonate. Alternatively, the desired products may be obtained by performing the same reaction using a cinnamyl derivative having a tertiary amino group, and thereafter quaternizing the product. As a consequence the non-quaternized tertiary amines corresponding to Formula I form an important aspect of the present invention.

The compounds may also be synthesized by the reductive alkylation, i.e., reduction of a substituted cinnamaldehyde and moranoline, or by reduction of these using a boron hydride complex. They can also be produced by preparing an amide from moranoline having protected hydroxyl groups and a substituted cinnamic acid, and reducing the amide.

The following examples will serve to further typify the nature of the invention. In these, the chloride anion is exemplified by the compounds of Examples 1 and 2. Because of the greater ease of crystallization, thus facilitating confirmation of chemical structure, the remaining compounds are isolated as the dipicrates. Other salts useful for this purpose include Reinecke's salt.

These examples should not be construed however as a limitation on the scope of the invention.

EXAMPLE 1

1-(3-Trimethylammoniumcinnamyl)-2-hydroxymethyl-3,4,5-trihydroxypiperidine Dichloride Fifteen (15) grams of m-dimethylaminobenzaldehyde is dissolved in 30 ml of tetrahydrofuran, and the solution is added dropwise to 100 ml of tetrahydrofuran containing about 15 g of vinyl magnesium bromide with stirring over the course of 10 minutes. After the addition, the mixture is stirred at 50° to 60° C. for 30 minutes. After cooling, a small amount of water is added to the reaction mixture for decomposition. The insoluble materials are removed by filtration, and the filtrate is concentrated under reduced pressure. The residue is extracted with ether to afford 16 g of the reaction product as a light yellow oil.

The product is dissolved in 100 ml of methanol, and 20 ml of methyl iodide is added. The mixture is heated under reflux for 1.5 hours. The reaction mixture is dried to a solid under reduced pressure, and the remaining crystalline substance is washed with ethanol. Amount yielded 22 g. The above crystals obtained (20 g) are dissolved in 200 ml of methanol and the solution is passed through a column of an ion-exchange resin [Dowex 1×2 (Br) about 500 ml]. The eluate is dried to a solid under reduced pressure, and the remaining crystalline substance is dissolved as such in 50 ml or conc. hydrobromic acid, and heated at 60° to 70° C. for 1 hour. Subsequently, the reaction mixture is evaporated to dryness under reduced pressure, and the residue is dissolved in water. Drying to a solid under reduced pressure is repeated to remove HBr completely. To the remaining yellowish brown glassy substance, 100 ml of DMSO having 10 g of moranoline dissolved therein is added. Then, 15 g of sodium hydrogen carbonate is added, and the mixture is stirred at room temperature for 2 hours. Then, the reaction mixture is filtered to remove insoluble materials. The product is diluted with 800 ml of water, and passed through a column of an ion-exchange resin [Dowex 50 W×4 (H) about 500 ml]. The column is washed with water, and the unreacted moranoline is eluted with 3% hydrochloric acid. Then, the column is eluted with 15% hydrochloric acid, and the eluate is dried to a solid under reduced pressure. The residue is dissolved in 200 ml of water, and a hot aqueous solution of sodium picrate is added until a precipitate no longer forms. The precipitate is collected by filtration, washed with water and isopropanol, and then added to 5% hydrochloric acid, followed by extraction with ethyl acetate until the yellow color disappears. The aqueous layer is evaporated to dryness completely under reduced pressure, and the remaining crystals are recrystallized from methanol. Hydrochloride.chloride: the amount yielded 7.4 g, melting point 202°–205° C., $[\alpha]_D^{24} = -15.2°$ (water).

EXAMPLE 2

By substituting p-dimethylaminobenzaldehyde in the procedure of Example 1, there is obtained 1-(4-trimethylammoniumcinnamyl)-2-hydroxymethyl-3,4,5-trihydroxypiperidine chloride hydrochloride, m.p. 186°–190° C., $[\alpha]_D^{24} = -15.5°$ (water).

Similarily prepared from p-diethylaminobenzaldehyde is 1-(4-methyldiethylammoniumcinnamyl)-2-hydroxymethyl-3,4,5-trihydroxypiperidine dipicrate, m.p. 133°–136° C., $[\alpha]_D^{24} = 14.3°$ (DMSO).

EXAMPLE 3

1-[3-(2-Triethylammoniumethoxy)cinnamyl[-2-hydroxymethyl-3,4,5-trihydroxypiperidine Dipicrate m-Diethylaminoethoxybenzaldehyde (6.8 g) is dissolved in 50 ml of tetrahydrofuran, and the solution is added dropwise to a solution of about 7 g of vinyl magnesium bromide in 60 ml of tetrahydrofuran with stirring. After the addition, the solution is heated to 50° C. for 30 minutes, and then cooled. A small amount of water is added to the reaction solution for decomposition. The insoluble materials are removed by filtration, and the filtrate is concentrated under reduced pressure. The residue is extracted with ether to obtain 8.0 g of the reaction product as a light yellow oil. The product is dissolved in 100 ml of methanol, and 20 g of ethyl iodide is added. The mixture is heated under reflux for 8 hours. The reaction mixture is dried to a solid under reduced pressure, and the remaining crystals are recrystallized from ethanol. Light yellow crystals (12 g) are obtained. The resulting crystals (11 g) is dissolved in 50 ml of methylene chloride, and 3.2 g of thionyl chloride is gradually added with stirring while cooling the solution with ice. The mixture is stirred at room temperature for 30 minutes. Then, the solvent is distilled off under reduced pressure, and the remaining yellowish brown glassy material is dissolved in 10 ml of DMSO. Moranoline (3 g) is dissolved in 25 ml of DMSO, and the solution is combined with the DMSO solution obtained above. Sodium hydrogen carbonate (5 g) is added, and the mixture is stirred overnight at room temperature. Then, the insoluble materials are removed by filtration. The filtrate is diluted with 200 ml of water, and passed through a column of an ion-exchange resin [Amberlite IR-120 (H) about 200 ml]. The column is washed with water and then eluted with 10% hydrochloric acid. The eluate is dried to a solid under reduced pressure, and the residue is dissolved in 50 ml of water. An excess of a hot aqueous solution of sodium picrate is added. A reddish brown resinous material which immediately precipitates is removed, and the residue is allowed to stand overnight at room temperature. Yellow crystals thus precipitate. They are recrystallized from a mixture of methanol and ethanol.

Dipicrate: melting point 116°–121° C. $[\alpha]_D^{24} = 13.0°$ (DMSO) Amount yielded 2.8 g.

EXAMPLE 4

Similarly prepared according to the procedure of Example 3 but from m-dimethylaminoethoxybenzaldehyde and m-dimethylaminopropoxybenzaldehyde are 1-[3-(2-trimethylammoniumethoxy)cinnamyl]-2-hydroxymethyl-3,4,5-trihydroxypiperidine dipicrate, m.p. 124°–127° C., $[\alpha]_D^{24} = +13.3°$ (DMSO) and 1-[3-(3-trimethylammoniumpropoxide)cinnamyl]-2-hydroxymethyl-3,4,5-trihydroxypiperidine dipicrate, m.p. 123°–126° C., $[\alpha]_D^{24} = +13.2$ (DMSO).

EXAMPLE 5

1-[3-(2-N-Methylmorpholiniumethoxy)cinnamyl]-2-hydroxymethyl-3,4,5-trihydroxypiperidine Dipicrate m-Morpholinoethoxybenzaldehyde (9.6 g) prepared from morpholinoethyl chloride and m-hydroxybenzaldehyde is dissolved in 20 ml of tetrahydrofuran. The solution is added dropwise to a solution of about 10 g of vinyl magnesium bromide in 50 ml of tetrahydrofuran. After the addition, the mixture is stirred at room temperature for 1.5 hours. Water is added for decomposition, and then the insoluble materials are removed by filtration. The filtrate is dried to a solid under reduced pressure, and the residue is extracted with ethyl acetate to obtain 8.9 g of the reaction product as a light yellow oil. The product is dissolved in 40 ml of methylene chloride, and 4.0 g of thionyl chloride is added dropwise with stirring while cooling the solution with ice. After the addition, the mixture is stirred at room temperature for 30 minutes. Then, it is dried to a solid at less than 30° C. under reduced pressure. The resulting reaction product as a yellowish brown oil is dissolved in 10 ml of DMF, and 45 ml of DMSO having 5.0 g of moranoline dissolved therein is added. Sodium hydrogen carbonate (10 g) is added, and the mixture is stirred at room temperature for 3 hours. After the reaction, the reaction mixture is diluted with 300 ml of water and alkalized with ammonia. Ammonium sulfate is added to salt out the product, followed by extraction with n-butanol. The extract is chromatographed on a silica gel column using a 2:1 mixture of chloroform and methanol to purify it and obtain 2.6 g of the product, 1-[3-(2-morpholinoethoxy)cinnamyl]-2-hydroxymethyl-3,4,5-trihydroxypiperidine, as a colorless oil.

This product is dissolved in 50 ml of methanol, and 3 g of methyl iodide is added. After standing at 0° C. for 10 hours, the reaction mixture is dried to a solid under reduced pressure. The residue is dissolved in 50 ml of water, and an excess of hot aqueous solution of sodium picrate is added. On standing in an ice chamber, crystals precipitate. They are recrystallized from methanol.

Dipicrate: melting point 170°–174° C. (decomp.) $[\alpha]_D^{24} = 1.0°$ (DMSO).

EXAMPLE 6

By substituting an equivalent amount of each of m-piperidineethoxybenzaldehyde and p-pyrrolidinoethoxybenzaldehyde in the procedure Example 5, there are respectively obtained 1-[3-(2-N-methylpiperidiniumethoxy)cinnamyl]-2-hydroxymethyl-3,4,5-trihydroxypiperidine dipicrate, m.p. 178°–185° C. (dec.), $[\alpha]_D^{24} = 2.5$ (DMSO), and 1-[4-(2-N-methylpyrrolidinoethoxy)cinnamyl]-2-hydroxymethyl-3,4,5-trihydroxypiperidine dipicrate, m.p. 184°–189° C. (dec.), $[\alpha]_D^{24} = 1.1$ (DMSO).

What is claimed is:

1. A compound of the formula:

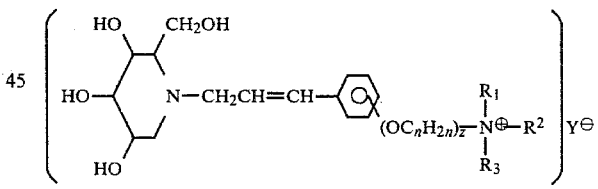

wherein
n has a value of 2 or 3,
z has a value of 0 or 1,
$R^1$ is alkyl of 1 to 6 carbon atoms, each of $R^2$ and $R^3$ is alkyl of 1 to 6 carbon atoms or
$R^2$ and $R^3$ when taken together, together with the nitrogen atom to which they are bound, are 1-morpholinylidene, 1-pyrrolidinylidene or 1-piperidinylidene; and
$Y^\ominus$ is a pharmaceutically acceptable cation.

2. A compound according to claim 1 in which z is 0.
3. A compound according to claim 2 in which each of $R^1$, $R^2$ and $R^3$ is the same or different alkyl group.
4. A compound according to claim 3 in which each of $R^1$, $R^2$ and $R^3$ is methyl or ethyl.
5. A compound according to claim 1 in which z is 1.
6. A compound according to claim 5 in which each of $R^1$, $R^2$ and $R^3$ is the same or different alkyl group.

7. A compound according to claim 6 in which each of $R^1$, $R^2$ and $R^3$ is methyl or ethyl.

8. A compound according to claim 5 in which n is 2.

9. A compound according to claim 8 in which $R^1$ is methyl and $R^2$ and $R^3$ together with the nitrogen atom to which they are attached are the 1,1-divalent residue of morpholine.

10. A compound according to claim 8 in which $R^1$ is methyl and $R^2$ and $R^3$ together with the nitrogen atom to which they are attached are the 1,1-divalent residue of piperidine.

11. A compound according to claim 8 in which $R^1$ methyl and $R^2$ and $R^3$ together with the nitrogen atom to which they are attached are the 1,1-divalent residue of pyrrolidine.

12. A compound of the formula:

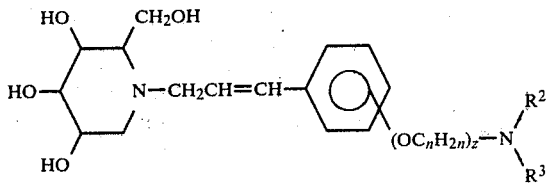

wherein
n has a value of 2 or 3,
z has a value of 0 or 1, and each of $R^2$ and $R^3$ is alkyl of 1 to 6 carbon atoms or
$R^2$ and $R^3$ when taken together, together with the nitrogen atom to which they are bound, are morpholino, pyrrolidino or piperidino.

* * * * *